US008292929B2

(12) United States Patent
Boschert

(10) Patent No.: US 8,292,929 B2
(45) Date of Patent: Oct. 23, 2012

(54) DYNAMIC SPINAL STABILIZATION SYSTEM AND METHOD OF USING THE SAME

(75) Inventor: Paul F. Boschert, Minneapolis, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 1167 days.

(21) Appl. No.: 11/687,014

(22) Filed: Mar. 16, 2007

(65) Prior Publication Data

US 2008/0234737 A1 Sep. 25, 2008

(51) Int. Cl.
*A61B 17/70* (2006.01)

(52) U.S. Cl. ...................................... 606/265

(58) Field of Classification Search .......... 606/246, 606/254–263, 264–277, 278–279, 86 A; 428/188
See application file for complete search history.

(56) References Cited

U.S. PATENT DOCUMENTS

| 4,950,269 | A | * | 8/1990 | Gaines, Jr. ................ 606/261 |
| 5,375,823 | A | | 12/1994 | Navas |
| 5,540,688 | A | | 7/1996 | Navas |
| 5,562,660 | A | | 10/1996 | Grob |
| 5,611,800 | A | | 3/1997 | Davis et al. |
| 5,725,582 | A | | 3/1998 | Bevan et al. |
| 5,961,516 | A | | 10/1999 | Graf |
| 5,989,250 | A | * | 11/1999 | Wagner et al. ............ 606/250 |
| 6,110,172 | A | * | 8/2000 | Jackson ...................... 606/305 |
| 6,241,730 | B1 | | 6/2001 | Alby |
| 6,290,700 | B1 | * | 9/2001 | Schmotzer ............... 606/263 |
| 6,743,231 | B1 | | 6/2004 | Gray et al. |
| 6,986,771 | B2 | | 1/2006 | Paul et al. |
| 6,989,011 | B2 | | 1/2006 | Paul et al. |
| 7,326,210 | B2 | * | 2/2008 | Jahng et al. .............. 606/86 A |
| 2002/0035366 | A1 | * | 3/2002 | Walder et al. ............ 606/61 |
| 2005/0065516 | A1 | | 3/2005 | Jahng |
| 2005/0085815 | A1 | | 4/2005 | Harms et al. |
| 2005/0124991 | A1 | | 6/2005 | Jahng |
| 2005/0143737 | A1 | | 6/2005 | Pafford et al. |
| 2005/0154390 | A1 | | 7/2005 | Biedermann et al. |
| 2005/0203513 | A1 | * | 9/2005 | Jahng et al. .............. 606/61 |
| 2006/0011715 | A1 | | 1/2006 | Bartlett et al. |
| 2006/0064092 | A1 | * | 3/2006 | Howland ................. 606/61 |
| 2006/0111715 | A1 | * | 5/2006 | Jackson ................... 606/61 |

(Continued)

FOREIGN PATENT DOCUMENTS

EP 0669109 A1 8/1995

(Continued)

*Primary Examiner* — Eduardo C Robert
*Assistant Examiner* — Steven Cotroneo
(74) *Attorney, Agent, or Firm* — Seager Tufte & Wickhem LLC

(57) ABSTRACT

A spinal stabilization system includes at least two anchors having a bone attachment portion and a head portion and a flexible assembly coupled to the anchors. The flexible assembly includes a flexible cord, at least two connectors slidably mounted to the flexible cord, and at least one spacer slidably mounted to the cord between adjacent connectors. Each connector couples with a head portion of an anchor. The flexible assembly may be assembled and appropriately adjusted outside the body prior to it being coupled to the anchors. In addition, the connectors may include angled outer surfaces that provide enhanced engagement with the ends of the spacer. A method of stabilizing the spine includes securing anchors to the spine, assembling a flexible assembly outside the body, and coupling the flexible assembly to the anchors. The method may further include providing connectors with angled surfaces to provide enhanced engagement with the spacer.

25 Claims, 3 Drawing Sheets

U.S. PATENT DOCUMENTS

| | | |
|---|---|---|
| 2006/0142758 A1 | 6/2006 | Petit |
| 2007/0016200 A1 | 1/2007 | Jackson |
| 2007/0055244 A1 | 3/2007 | Jackson |
| 2007/0129729 A1 | 6/2007 | Petit et al. |
| 2007/0198088 A1 | 8/2007 | Biedermann et al. |
| 2007/0270860 A1 | 11/2007 | Jackson |
| 2007/0293862 A1 | 12/2007 | Jackson |
| 2008/0091213 A1 | 4/2008 | Jackson |
| 2008/0140076 A1 | 6/2008 | Jackson |
| 2008/0147122 A1 | 6/2008 | Jackson |
| 2008/0177317 A1* | 7/2008 | Jackson .................. 606/254 |
| 2008/0183216 A1* | 7/2008 | Jackson .................. 606/278 |

FOREIGN PATENT DOCUMENTS

| | | |
|---|---|---|
| EP | 0669109 B1 | 8/1995 |
| EP | 0669109 B1 | 5/1999 |
| EP | 1523949 A1 | 4/2005 |
| EP | 1523949 B1 | 6/2007 |
| FR | 2676911 A1 | 12/1992 |
| FR | 2715057 A1 | 7/1995 |
| FR | 2730405 A1 | 8/1996 |
| FR | 2755844 A1 | 7/2001 |
| FR | 2844180 A1 | 3/2004 |
| FR | 2867057 A1 | 9/2005 |
| NL | 7610576 | 3/1978 |
| WO | 9417745 A1 | 8/1994 |
| WO | 9519149 A1 | 7/1995 |
| WO | 9905980 A1 | 2/1999 |
| WO | 9944527 A1 | 9/1999 |
| WO | 2004024011 A1 | 3/2004 |
| WO | 2005087121 A1 | 9/2005 |
| WO | 2006066685 A1 | 6/2006 |

* cited by examiner

DYNAMIC SPINAL STABILIZATION SYSTEM AND METHOD OF USING THE SAME

FIELD OF THE INVENTION

The present invention generally relates to spinal support devices, and more particularly to an apparatus and method for dynamically stabilizing the spine.

BACKGROUND OF THE INVENTION

The spinal column is a highly complex system of bones and connective tissues that provides support for the body and protects the delicate spinal cord and nerves. The spinal column includes a series of vertebrae stacked one on top of the other, each vertebral body including a portion of relatively weak cancellous bone and a portion of relatively strong cortical bone. Situated between each vertebral body is an intervertebral disc that cushions and dampens compressive forces experienced by the spinal column. A vertebral canal containing the spinal cord and nerves is located posterior to the vertebral bodies. In spite of the complexities, the spine is a highly flexible structure, capable of a high degree of curvature and twist in nearly every direction. For example, the kinematics of the spine normally includes flexion, extension, rotation and lateral bending.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in the lumbar or cervical spine), and other disorders caused by abnormalities, disease, or trauma, such as ruptured or slipped discs, degenerative disc disease, fractured vertebra, and the like. Patients that suffer from such conditions usually experience extreme and debilitating pain, as well as diminished nerve function. These spinal disorders, pathologies, and injuries limit the spine's range of motion, or threaten the critical elements of the nervous system housed within the spinal column.

The treatment of acute and chronic spinal instabilities or deformities of the thoracic, lumbar, and sacral spine has traditionally involved rigid stabilization. For example, arthrodesis, or spine fusion, is one of the most common surgical interventions today. The purpose of fusion or rigid stabilization is the immobilization of a portion of the spine to affect treatment. Rigid stabilization typically includes implantation of a rigid assembly having metallic rods, plates and the like that secure selective vertebrae relative to each other. Spinal treatment using rigid stabilization, however, does have some disadvantages. For example, it has been shown that spine fusion decreases function by limiting the range of motion for patients in flexion, extension, rotation and lateral bending. Furthermore, it has been shown that spine fusion creates increased stresses and therefore, accelerated degeneration of adjacent non-fused segments. Another disadvantage of fusion is that it is an irreversible procedure.

More recently, dynamic stabilization has been used in spinal treatment procedures. Dynamic stabilization does not result in complete spinal fusion but instead permits enhanced mobility of the spine while also providing sufficient stabilization to effect treatment. One example of a dynamic stabilization system is the Dynesys® system available from Zimmer Spine, Inc. of Edina, Minn. Such dynamic stabilization systems typically include a flexible spacer positioned between pedicle screws installed in adjacent vertebrae of the spine. Once the spacer is positioned between the pedicle screws, a flexible cord is threaded through eyelets formed in the pedicle screws and a channel through the spacer. The flexible cord retains the spacer between the pedicle screws while cooperating with the spacer to permit mobility of the spine.

Many current dynamic stabilization systems are typically assembled in situ. In these systems, a surgical site is established in the patient and a pair of bone anchors is coupled to adjacent vertebrae. Spacers are then inserted into the surgical site and positioned between the anchors while a flexible cord is threaded through the anchors and spacers, generally in a direction parallel to the axis of the spine, to assemble the device in the body. Once the stabilization system is assembled, the appropriate amount of pre-tensioning must be applied to the cord and other post-assembly adjustments must be made to effect spinal treatment.

While dynamic stabilization systems are generally successful for treating various spinal conditions, manufacturers or providers of such stabilization systems continually strive to improve these stabilization systems. By way of example, manufacturers or providers strive to provide relatively quick and convenient assembly and installation of the stabilization system. For example, minimally invasive surgical techniques often utilize much smaller incisions and provide the benefits of less tissue and muscle displacement and quicker recovery.

Manufacturers or providers of stabilization systems also strive to provide systems that transmit imposed loads on the spine through the system and to the underlying bone structure in an efficient and effective manner. In such applications, for example, engagement of the spacers with the connectors on the anchors should provide for optimal transmission of the loads imposed on the stabilization systems to the underlying bone structure. Ideally, when the stabilization system is assembled, the end faces of the spacer will substantially mate with the surfaces of the eyelet so as to maximize the contact area between the spacer and the anchor.

If the contact between the ends of the spacer and the surfaces of the eyelets occurs at less than the full contact area results, then such a reduction in contact area between the components localizes the load transfer. This may be due to the specific vertebral physiology to which the stabilization system is being applied, the geometry of the components or the non-idealized placement of the anchors in the vertebrae. In any event, the resulting reduction in contact area between the spacer and anchors may diminish the capacity of the stabilization system to efficiently transmit applied loads to the vertebrae to which the anchors are attached. This may result in a reduction in the support provided by the stabilization system, a loss of the pre-tensioning of the system, or otherwise affect the stabilization system in a manner that impacts treatment of the spine.

Accordingly, there is a need for an improved dynamic stabilization system and method of using the same that addresses these objectives.

SUMMARY OF THE INVENTION

A dynamic stabilization system that provides improvements over existing stabilization systems includes at least two vertebral anchors having a bone attachment portion and a head portion. The vertebral anchors might be, for example, bone screws. Each of the vertebral anchors is adapted to be coupled to different vertebrae of the spine. A flexible assembly is removably coupled to the vertebral anchors and includes a flexible cord, at least two connectors slidably mounted to the flexible cord, and at least one spacer slidably mounted to the cord. Each of the connectors is adapted to be coupled with a head portion of a respective anchor. Moreover, the flexible assembly is configured such that each spacer is disposed between adjacent connectors. In one aspect of the invention, the spatial relationship of the connectors on the flexible assembly are capable of being fixed relative to the cord prior to the flexible assembly being coupled to the vertebral anchors. This aspect may allow, for example, the flexible assembly to be assembled outside the body of a patient and then subsequently coupled to the anchors in situ.

In one embodiment, for example, each of the connectors includes a channel extending through the connector for receiving the cord therein. Each connector further includes a threaded bore extending from a surface of the connector and intersecting the channel. A set screw is threadably engaged with the bore and cooperates therewith so as to prevent relative movement between the cord and connector when the connector is mounted on the cord.

In another embodiment, the stabilization system includes at least two vertebral anchors having a bone attachment portion generally defining an axis, wherein each of the anchors is adapted to be coupled to different vertebrae of the spine. A flexible cord extends between the anchors. The system further includes at least two connectors, each connector adapted to be coupled to the bone attachment portion of one of the vertebral anchors and to the flexible cord. A first spacer is disposed between adjacent connectors and includes a channel for receiving the cord therethrough. The first spacer includes first and second opposed end faces. At least one of the connectors includes a first outer surface that confronts the first end face of the first spacer. In another aspect of the invention, the first outer surface of the at least one connector forms an angle with respect to the axis of the bone attachment portion of the vertebral anchor. Angulation of the first outer surface enhances the contact area between the first outer surface of the at least one connector and the first end face of the first spacer. This aspect may allow, for example, improved transmission of loads through the stabilization system and to the vertebrae to which the system is attached.

By way of example, in one embodiment the at least one connector includes a lower surface and an upper surface, and the first outer surface is angled inwardly toward the axis of the bone attachment portion in a direction from the lower surface toward the upper surface. In another embodiment, however, the first outer surface is angled outwardly away from the axis of the bone attachment portion in a direction from the lower surface toward the upper surface. In still another embodiment, the at least one connector includes a second outer surface that confronts an end face of a second spacer. The second outer surface likewise forms an angle with respect to the axis of the bone attachment portion so as to enhance the contact area between the second outer surface and the end face of the second spacer. Depending on the specific application, the angulation of the first and second outer surfaces may be the same or may be different from each other.

In yet another embodiment, a spinal stabilization system includes a vertebral anchor having a bone attachment portion and a head portion. The anchor is adapted to be coupled to a vertebra of the spine. The head portion includes a base member coupled to the bone attachment portion at one end thereof and a pair of spaced apart legs extending from the base member. The base member and legs collectively define an open channel in the head portion. The stabilization system further includes an assembly having a connector for removably coupling the assembly to the anchor. The connector includes first and second body portions and a narrowed intermediate body portion extending between the first and second body portions. The first, second and intermediate body portions collectively define a pair of opposed cutouts that receive the legs of the head portion therein when the connector is coupled to the anchor. When the connector is so coupled to the anchor, the intermediate body portion is received in the open channel of the head portion.

In one embodiment, each of the legs projects from the base member at an angle of approximately 90 degrees. In such an embodiment, the intermediate body portion may likewise be configured so as to be closely received in the open channel. Accordingly, a pair of side surfaces of the intermediate body portion may project from a lower surface thereof at an angle of approximately 90 degrees. In another embodiment, however, the open channel and intermediate body portion may have a converging configuration to provided a snap-fit feature between the two. Thus, each of the legs projects from the base member at an angle between approximately 85 degrees and 90 degrees. Similarly, the side surfaces of the intermediate body portion may project from the lower surface thereof at an angle between approximately 85 degrees and 90 degrees. Furthermore, the stabilization system may include a retaining mechanism for selectively retaining the connector with the anchor. To this end, the system may include a retaining clip that is applied to the ends of the legs opposite the base member. Each of the legs, for example, may include a retaining notch that receives a portion of the retaining clip therein. When the retaining clip is positioned in the retaining notches on the legs, the legs are prevented from moving away from each other and the connector is prevented from moving away from the anchor.

A method of stabilizing a spine within a body of a patient includes securing at least first and second anchors to respective first and second vertebrae of the spine, assembling a flexible assembly outside the body, adjusting the flexible assembly outside the body such that the flexible assembly is capable of stabilizing the spine once disposed inside the body, and removably coupling the flexible assembly to the anchors to stabilize the spine. In such a method, assembling the flexible assembly may include slidably mounting at least two connectors onto a flexible cord and/or slidably mounting at least one spacer on the cord so as to be positioned between the connectors. Moreover, adjusting the flexible assembly may include pre-tensioning the flexible cord, spatially fixing the connectors relative to the cord, and/or adjusting the length of the spacer.

A method of stabilizing the spine in accordance with an alternate embodiment of the invention includes securing at least first and second anchors to respective first and second vertebrae of the spine, and providing a plethora of connectors for coupling a flexible assembly to the anchors. The flexible assembly includes at least one spacer with first and second opposed end faces. The connector has at least a first outer surface that forms an angle with respect to an axis of the anchor when coupled thereto. The method further includes determining the angle of the first outer surface so that the first outer surface engages substantially all of one of the end faces of the spacer when the flexible assembly is coupled to the spine; constructing the flexible assembly using a connector having a first outer surface with the determined angle; and then coupling the flexible assembly to the anchors to stabilize the spine.

These and other objects, advantages and features of the invention will become more readily apparent to those of ordinary skill in the art upon review of the following detailed description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
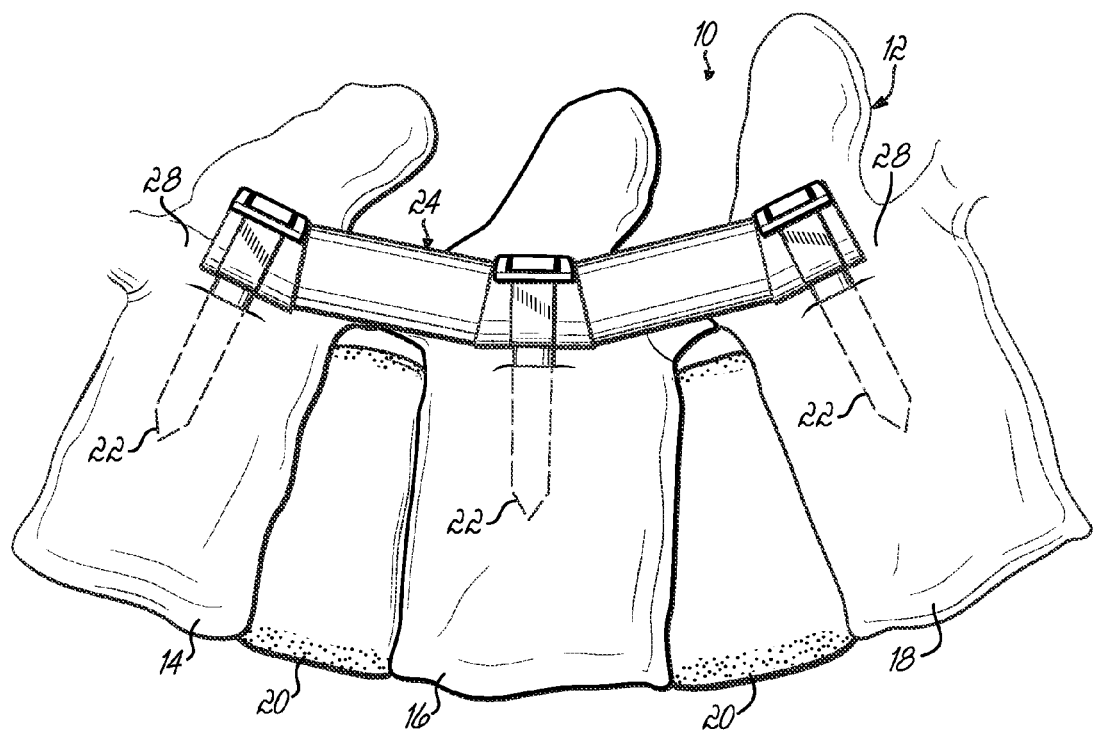
FIG. 1 is a side elevation view of an exemplary stabilization system in accordance with an embodiment of the invention implanted on the spine.

Referring now to the drawings, and to FIG. 1 in particular, a spinal stabilization system 10 is shown implanted into a segment of a spine 12 defined by serially positioned spinal elements in the form of adjacent vertebrae 14, 16, 18 that are separated by discs 20. The stabilization system 10 includes anchors 22 installed in vertebrae 14, 16, 18 and a flexible assembly 24 coupled to and extending between the anchors 22 to control abnormal motion of the spine 12, while otherwise leaving the spinal segment mobile.

Figure 2:
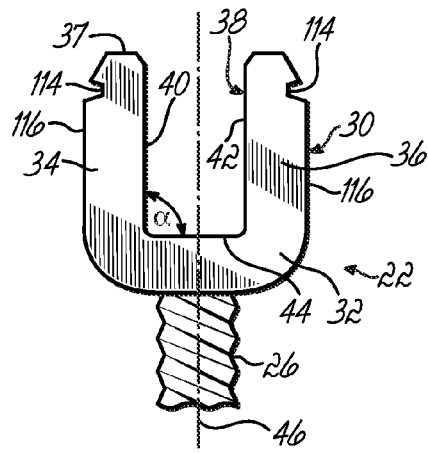
FIG. 2 is a front view of a bone anchor in accordance with an embodiment of the invention.

FIG. 2 illustrates an exemplary embodiment of an anchor used in the spinal stabilization system 10 in more detail. As shown in this figure, each anchor 22 may be configured as a pedicle bone screw having a threaded portion 26 adapted to facilitate coupling between the anchor 22 and the pedicle 28 (FIG. 1) of the vertebrae 14, 16, 18 and a head portion 30 adapted to couple to the flexible assembly 24. While pedicle screws are shown and described herein, those of ordinary skill in the art will appreciate that the spinal anchors 22 may take the form of hooks or other devices coupled to the spine 12.

As best illustrated in FIG. 2, the head portion 30 of the anchors 22 define a U-shaped receiving portion having a base member 32 from which threaded portion 26 projects, and a pair of legs 34, 36 each having a first end coupled to the base member 32 and a second end 37 spaced from base member 32. The base member 32 and legs 34, 36 collectively define a U-shaped channel 38 defined by side surfaces 40, 42, and base surface 44. The channel 38 is open along a top or posterior end (relative to the pedicle 28) so as to receive a portion of the flexible assembly 24 in a top-load manner. The anchors 22 may be formed from any suitable material including, for example and without limitation, titanium, stainless steel, or other materials recognized by those of ordinary skill in the art.

The legs 34, 36 may project from base member 32 such that the side surfaces 40, 42 form an angle α with base surface 44 of approximately 90 degrees, i.e., the base surface 44 and side surfaces 40, 42 are orthogonal to each other. Alternately, the angle α may be less than 90 degrees, such as between approximately 80 and 90 degrees, and more preferably between 85 and 90 degrees, so that the legs 34, 36 converge toward an axis 46 of threaded portion 26 in a direction away from base surface 44. As explained in more detail below, such a converging configuration of the receiving portion facilitates coupling of the flexible assembly 24 to the anchors 22. In such an embodiment, the legs 34, 36 may be formed of a suitable material that provides some flexibility or resiliency to the legs 34, 36 toward and away from each other. For example, titanium would provide sufficient flexibility to legs 34, 36.

Figure 3:
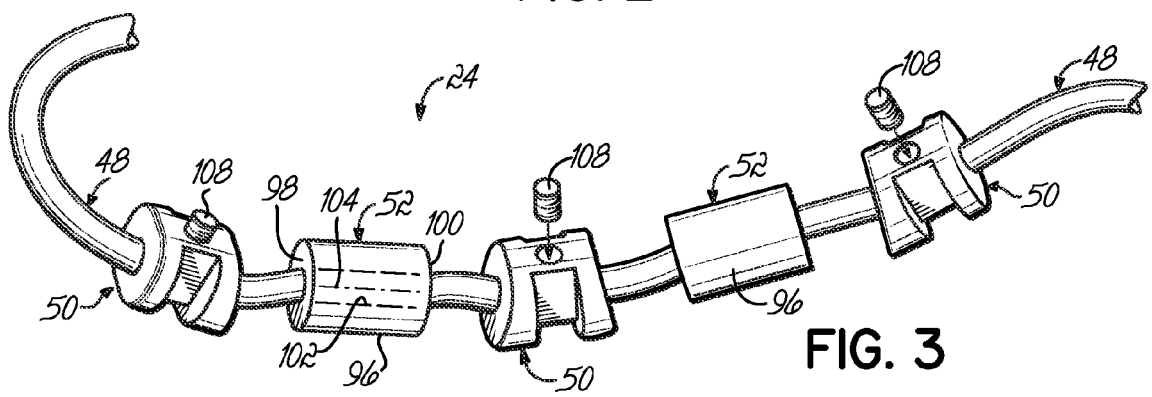
FIG. 3 is a perspective view of a flexible assembly in accordance with an embodiment of the invention.

FIG. 3 illustrates an embodiment of a flexible assembly 24 in accordance with the invention. The flexible assembly 24 includes a generally flexible cord 48 capable of flexing in substantially all directions and is further capable of having one portion of the cord rotated relative to another portion of the cord, i.e., the cord 48 is capable of being twisted. Moreover, the cord 48 is further capable of withstanding and maintaining tension within the cord 48. Such a cord 48 may be formed, for example and without limitation, from polyethylene terephthalate (PET), titanium or other metal materials, or other suitable materials recognized by those of ordinary skill in the art. The cord 48 may also have any desirable cross section, such as and without limitation, circular, rectangular, triangular, etc. The flexible assembly 24 further includes at least two connectors 50 and at least one spacer 52 mounted on the cord 48.

Those of ordinary skill in the art will recognize that the number of connectors 50 typically corresponds to the number of anchors 22 coupled to the vertebrae. Moreover, spacers 52 are typically positioned between adjacent connectors 50. Thus, while FIGS. 1 and 3 illustrate a stabilization system 10 having three anchors 22, three connectors 50, and two spacers 52, the invention is not so limited as fewer or more anchors 18, connectors 50 and spacers 52 may be used to construct the stabilization system 10, as dictated by the specific application. The connectors 50 and spacers 52 will now be described in detail.

Figure 4A:
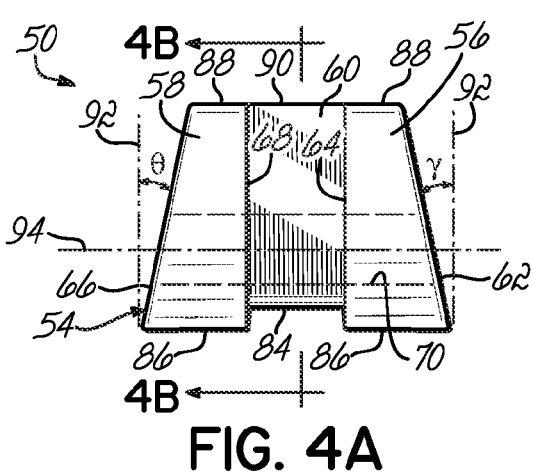
FIG. 4A is a side view of a connector used in the flexible assembly shown in FIG. 3.
Figure 4B:
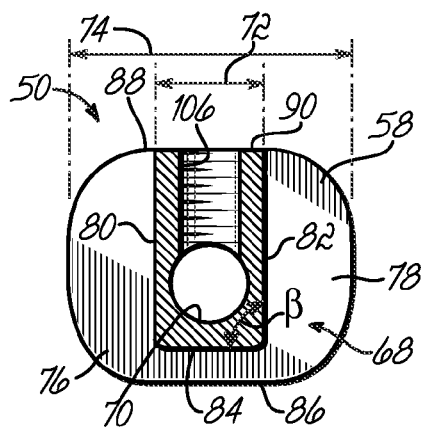
FIG. 4B is a cross-sectional view of the connector shown in FIG. 4A taken generally along line 4B-4B.

As shown in FIGS. 3, 4A-4C, in one embodiment, each connector 50 includes a generally cylindrical body 54 including a first body portion 56, a second body portion 58, and a narrowed intermediate body portion 60 that connects the first and second body portions 54, 56. The body 54 may be formed out of suitable materials, such as, for example and without limitation, titanium, stainless steel, a polymeric material, or other suitable materials known to those of ordinary skill in the art. The first body portion 56 includes an outer surface 62 and an inner surface 64, and second body portion 58 similarly includes an outer surface 66 and an inner surface 68. The body portions 56, 58 are configured such that the inner surfaces 64, 68 face each other and are each coupled to an end of intermediate portion 60. The body 54 includes a longitudinal channel 70 formed through the first, second and intermediate body portions 56, 58, 60 so as to closely, but yet slidably, receive cord 48 therethrough. Additionally, channel 70 may have a cross section that corresponds to the cross section of cord 48. Thus, while a circular cross section is shown in FIG. 4B, those of ordinary skill in the art will recognize other cross sections, such as rectangular, triangular, etc., are within the scope of the invention.

Figure 4C:
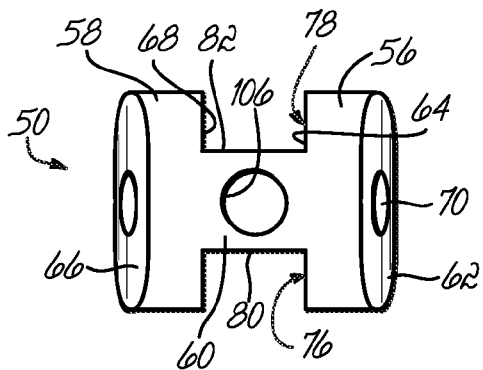
FIG. 4C is a top view of the connector shown in FIG. 4A.

The intermediate body portion 70 has a maximum cross dimension 72 in a lateral direction (FIG. 4B) that is less than or equal to the cross dimension 74 of the inner surfaces 64, 68 of the first and second body portions 56, 58 to define a pair of U-shaped cutouts 76, 78 on opposed sides of the intermediate body portion 60 (FIG. 4C). The cutouts 76, 78 are each defined by portions of the inner surfaces 64, 68 and respective side surfaces 80, 82 on the intermediate body portion 60. The cutouts 76, 78 are configured to receive the legs 34, 36 of head portion 30 of anchors 22 therein. In addition, the intermediate body portion 60 includes a lower surface 84 that is spaced from the lower surface 86 of the first and second body portions 56, 58 and toward an upper surface 88 of the body portions 56, 58. An upper surface 90 of the intermediate body portion 60 may be generally flush with the upper surface 88 of the first and second body portions 56, 58, although not so limited.

The intermediate body portion 60 on each of the connectors 50 is configured to fit within the U-shaped channel 38 in the head portion 30 of a corresponding anchor 22. In this regard, the lower surface 84 of the intermediate body portion 60 engages the base surface 44 of base member 32 and the side surfaces 80, 82 of intermediate body portion 60 are closely received within the side surfaces 40, 42 of the legs 34, 36. The surfaces 80, 82, and 84 of intermediate body portion 60 define a shape generally corresponding to the shape of channel 34. For example, the side surfaces 80, 82 may form an angle β with the lower surface 84 of approximately 90 degrees when the side surfaces 40, 42 are generally orthogonal to base surface 44.

In an alternate embodiment, however, the side surfaces 80, 82 may have a converging relationship such that the angle β is less than 90 degrees, such as between approximately 80 and 90 degrees, and more preferably between 85 and 90 degrees, so that the surfaces 80, 82 converge toward one another in a direction from lower surface 84 to upper surface 90. The angle β is typically equal to the angle α so that the side surfaces 40, 42 of the legs 34, 36 mate with the side surfaces 80, 82 of intermediate body portion 60 over a substantial portion of the contact area between the two. As discussed in more detail below, the converging feature to the mating side surfaces of the legs 34, 36 and the intermediate body portion 60 provide a snap-fit type of feature between the flexible assembly 24 and the anchors 22.

As noted above, in some prior applications the contact area between the connectors and spacers may be reduced which in turn reduces the efficiency that loads are transmitted through the stabilization system and to the vertebrae. To improve load transmission in these cases, the outer surfaces 62, 66 of the first and second body portions 56, 58 of the connectors 50 may be angled. For example, as best shown in FIG. 4A, the outer surfaces 62, 66, form angles γ, θ with respect to planes 92 that are generally orthogonal to an axis 94 extending along channel 70. Stated in an alternate way, the outer surfaces 62, 66 may form angles γ, θ with respect to the axis 46 of the threaded portion 26 of anchors 22 when the connectors 50 are coupled to the anchors 22. While the angles γ, θ are shown as being substantially equal, the invention is not so limited as the angles may be different from each other.

Moreover, while the connector 50 in FIG. 4A shows the outer surfaces 62, 66 as being angled inwardly, i.e., toward the opposed outer surface, in a direction from the lower surface 86 toward the upper surface 88, one or both of the outer surfaces 62, 66 may be angled outwardly, i.e., away from the opposed outer surface, in a direction from the lower surface 86 toward the upper surface 88. Thus, a plurality of connectors 50 with various angular configurations of the outer surfaces 62, 66 may be provided to accommodate the construction of a stabilization system that meets a specific application so as to provide excellent load transmission to the vertebrae.

As shown in FIG. 3, the spacers 52 include a generally cylindrical body 96 having a first end defining a first end face 98, a second opposed end defining a second end face 100, and a longitudinal channel 102 extending between and through the end faces 98, 100, as is conventional. The channel 102 is configured to closely, but yet slidably, receive cord 48 therethrough. Moreover, channel 102 may have a cross section that corresponds to the cross section of cord 48 and may be circular, rectangular, triangular, etc. The spacers 52 maintain the distraction between adjacent vertebrae, such as vertebrae 14, 16, 18, while also providing some flexibility to the stabilization system 10 for enhanced mobility of the spine 12. For example, the spacers 52 may be formed from polycarbonate urethane (PCU) or other suitable materials recognized by those of ordinary skill in the art. Furthermore, and as is conventional, the end faces 98, 100 may be generally orthogonal to a longitudinal axis 104 of the spacer 52.

Figure 5:
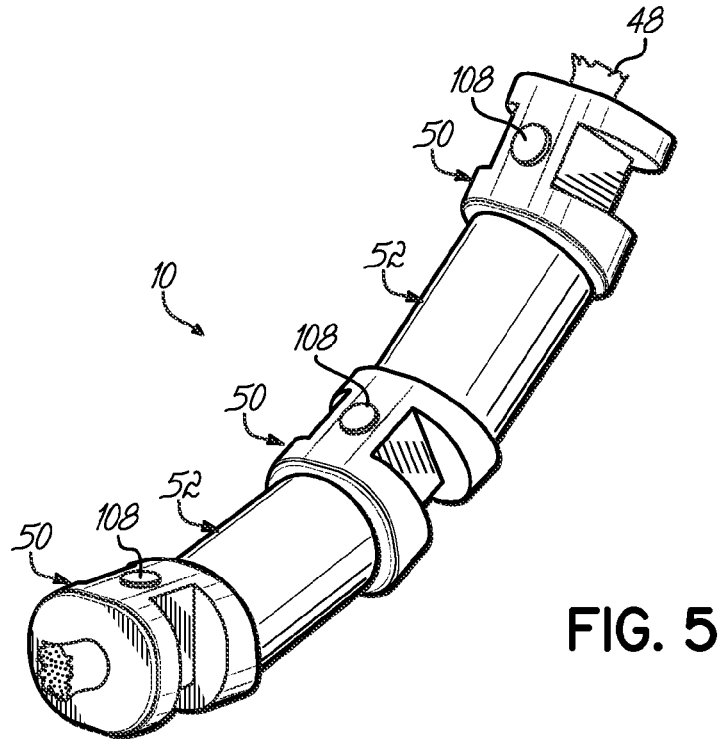
FIG. 5 is a perspective view of the flexible assembly of FIG. 3 ready for insertion into the body.

Use of the stabilization system 10 in accordance with the invention will now be described in detail in reference to FIGS. 3, 5 and 6. To install the stabilization system 10 to the spine 12, the anchors 22 are secured to the selected vertebrae 14, 16, 18 of the spine 12. For example, the threaded portion 26 of the bone screw may be secured within the vertebrae as is known in the art. As noted above, due to vertebral physiology, non-idealized placement of the anchors 22 and/or other reasons, the outer surfaces 62, 66 of the connectors 50 may require some angulation to ensure improved contact between the spacers 52 and connectors 50. Once the anchors 22 have been secured to the vertebrae 14, 16, 18, the angles γ, θ of the outer surfaces 62, 66 of each of the connectors 50 may be calculated or determined, in a manner generally known in the art, that will provide increased contact between the end faces 98, 100 of spacers 52 and the outer surfaces 62, 66 of the connectors 50.

Once the angles for the outer surfaces 62, 66 of each of the connectors 50 have been determined, the flexible assembly 24 may be constructed. In one aspect of the invention, because the connectors 50 are separate elements or components from the anchors 22, the flexible assembly 24 may be constructed prior to being inserted into the patient through the surgical site. Thus, as shown in FIG. 4, the connectors 50 (having the pre-determined angulation of their outer surfaces), and spacers 52 may be slidably mounted on the cord 48. In addition, the various adjustments to the flexible assembly 24 to effect treatment of the spine 12 may be made thereto prior to the insertion of the flexible assembly into the patient. Thus, for example, the length of the spacers 52, the relative positions of the connectors 50, the tension in the cord 48, and/or other design features may all be set while the flexible assembly 24 is outside the body of the patient.

In this regard, the connectors 50 may be secured relative to the cord 48 so as to spatially fix the components of the flexible assembly 24. To this end, and as best shown in FIG. 4B, each of the connectors 50 include a threaded bore 106 that extends from the upper surface 90 of the connector body 54 to the channel 70 that receives the cord 48 therethrough. As shown in FIG. 3, a set screw 108 is received in the threaded bore 106 and may be rotated in a conventional manner so that an end of the set screw 108 engages the cord 48 to secure the connector 50 thereto and prevent relative movement therebetween. Accordingly, as illustrated in FIG. 5, the design configuration of the flexible construct 24 may be completed outside the body of the patient. Moreover, FIG. 5 also illustrates that in the design configuration, i.e., the pre-tensioning of the cord 48, length of spacers 52, etc. have all been completed, the end faces 98, 100 of the spacers 52 mate with the outer surfaces 62, 66 of the connectors 50 over a relatively large contact area. For example, the end faces 98, 100 mate with the outer surfaces 62, 66 of the connectors 50 over substantially the entire surface area of the end faces 98, 100. The enhanced contact area provides improved load transmission through the stabilization system 10 and to the vertebrae 14, 16, 18 to which the system is attached.

Once the flexible assembly 24 has been constructed and configured for operation with the stabilization system 10, the flexible assembly 24 may be removably coupled to the anchors 22, which have already been coupled to the vertebrae, to complete the construction of the stabilization system 10. To this end, and in another aspect of the invention, the flexible construct 24 may be coupled to the anchors 22 in a top load manner. In reference to FIGS. 1 and 6, the connectors 50 on the flexible assembly 24 are aligned with the U-shaped head portions 30 of the anchors 22 and moved downward in a generally anterior direction relative to the spine 12. As the flexible assembly 24 is moved in the anterior direction, the legs 34, 36 of the head portions 30 engage the cutouts 76, 78 so that the intermediate body portion 60 of the connectors 50 is seated within the channel 38 of the head portions 30.

When the side surfaces 40, 42 of the legs 34, 36 are orthogonal to the base surface 44 and the side surfaces 80, 82 of the intermediate body portion 60 are orthogonal to lower surface 84, the channel 38 closely receives the intermediate body portion 60. However, when the channel 38 and intermediate body portion 60 have the converging configuration as discussed above, the legs 34, 36 initially flex outward as the connectors 50 are moved into the channels 38. As the connectors 50 are further moved in the anterior direction, however, the legs 34, 36 spring back to essentially pull the connectors 50 into the channels 38 in a snap-fit manner. Moreover, because the legs 34, 36 converge, the legs 34, 36 at least provisionally secure the connectors 50 with the anchors 22 to provide some level of resistance to the movement of the connectors 50 in a posterior direction and away from the anchors 22.

Figure 6:
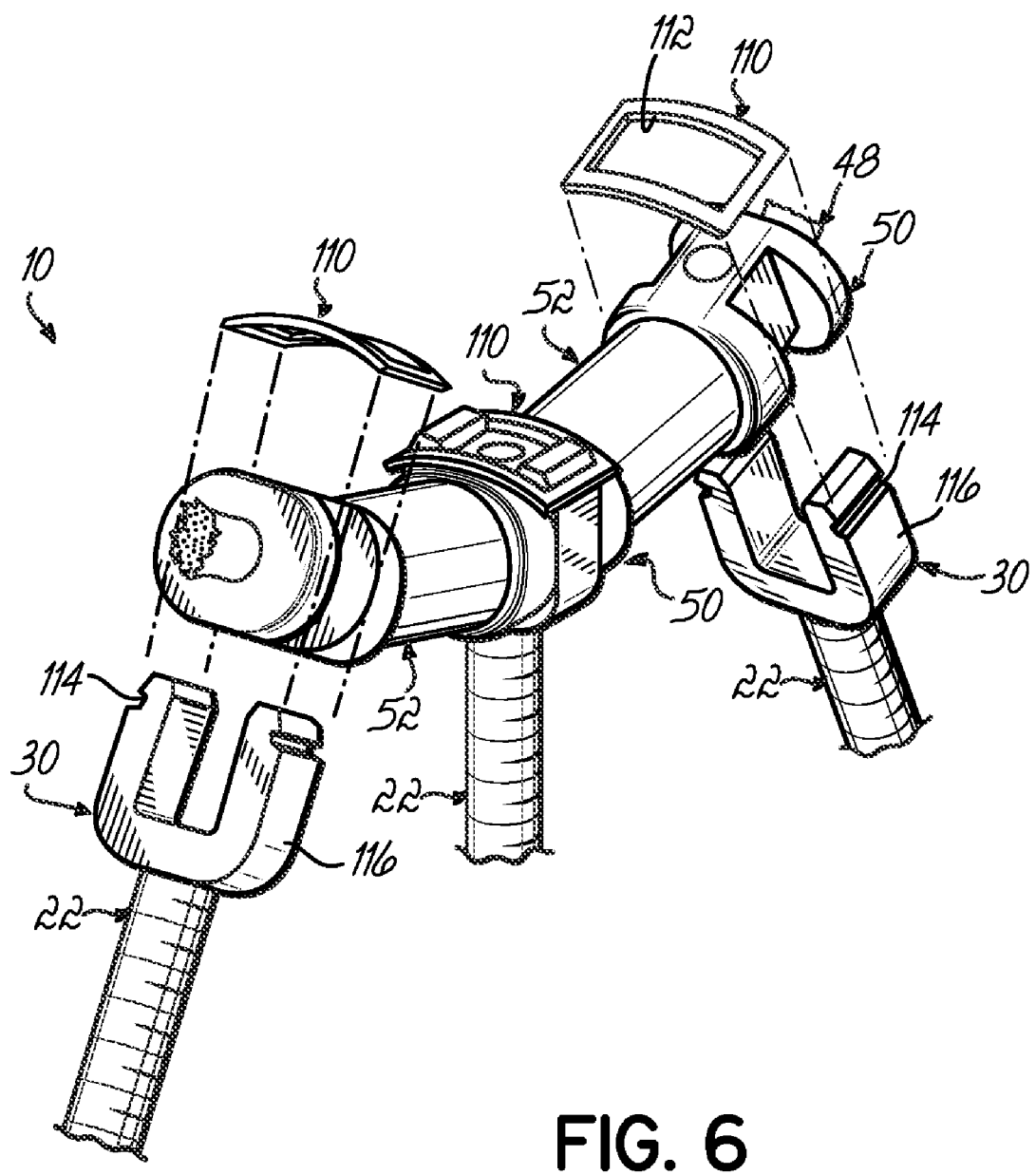
FIG. 6 is a perspective view illustrating the coupling between the flexible assembly and the anchors.

As illustrated in FIGS. 2 and 6, when the connectors 50 of the flexible assembly 24 are positioned within the channels 38 of the head portions 30 of the anchors 22, the connectors 50 may be secured or further secured with the anchors 22 to prevent any relative movement of the connectors 50 relative to the anchors 22. To this end, a retainer in the form of a retaining clip 110 may be used to achieve the securement of the connectors 50 to the anchors 22. The retaining clip 110 may be generally rectangular having a rectangular aperture 112 that receives the second ends 37 of the legs 34, 36 therethrough. To secure the retaining clip 110 to the ends 37 of the legs 34, 36, the legs 34, 36 may include retaining notches 114 along outer side surfaces 116. Other retainers include screws, bolts, pins, adhesives and the like.

In this way, when a connector 50 is positioned in the channel 38 of head portion 30 of anchor 22, the second ends 37 of legs 34, 36 may be squeezed or pushed together so as to be inserted through the aperture 112 in retaining clip 110. Once through the aperture 112, the legs 34, 36 may be released so that the side edges of the clip 110 are positioned in the retaining notches 114. When so coupled, the retaining clip 110 is adjacent the upper surface 88 of the connector 50 and prevents movement of the connector 50 in a posterior direction away from the anchor 22.

Embodiments of the stabilization system as described herein and in accordance with the invention provide a number of improvements over current stabilization systems. For example, embodiments of the invention permit the flexible assembly 24 to be constructed outside the body of the patient and then subsequently coupled to the anchors in situ. Such an arrangement allows the pre-tensioning of the cord, spacer length, and other design aspects of the flexible assembly to be done prior to insertion into the body. This may facilitate the use of such dynamic stabilization systems with minimally invasive surgical techniques and therefore gain the benefits of those surgical techniques.

Embodiments of the invention described herein also improve the load transmission efficiency of dynamic stabilization systems in those cases where ideal contact between the connectors and spacers may not be achieved. By selectively angling the surfaces of the connectors, the contact area between the spacers and connectors may be enhanced to improve the ability of the stabilization systems to transmit loads to the underlying vertebrae to which the systems are attached.

While the present invention has been illustrated by a description of various preferred embodiments and while these embodiments have been described in some detail, it is not the intention of the inventor to restrict or in any way limit the scope of the appended claims to such detail. Additional advantages and modifications will readily appear to those skilled in the art. The various features of the invention may be used alone or in numerous combinations depending on the needs and preferences of the user.

What is claimed is:

1. A spinal stabilization apparatus, comprising:
a least two vertebral anchors, each vertebral anchor having a bone attachment portion and a head portion, the head portion including a base portion and a pair of spaced apart legs extending from the base portion to an upper extent of the legs and defining a channel therebetween, each vertebral anchor securable to a respective vertebra of a spine;
a flexible assembly removably securable to the vertebral anchors, the flexible assembly comprising:
a flexible element;
at least two connectors positionable on the flexible element for coupling with the head portions of respective vertebral anchors, wherein each connector includes a first body portion, a second body portion, an intermediate body portion extending between the first body portion and the second body portion, and a bore having a longitudinal axis which extends through each of the first body portion, the second body portion, and the intermediate body portion, the intermediate body portion configured to be received in the channel of a respective vertebral anchor with the first and second body portions positioned exterior to and on opposing sides of the head portion such that the upper extent of the legs are positioned above an upper extent of the connector when the connector is engaged against the base portion; and
at least one spacer positionable on the flexible element between adjacent connectors, wherein the spacer includes a bore having a longitudinal axis;
wherein the longitudinal axis of the spacer is non-parallel to the longitudinal axis of at least one of the connectors when a face of the spacer is in abutting contact with a face of one of the connectors;
wherein the spatial relationship of the connectors are capable of being fixed relative to the flexible element prior to the flexible assembly being coupled to the vertebral anchors.

2. The spinal stabilization apparatus of claim 1, wherein each of the connectors is slidable relative to the flexible element and the flexible element is received through the bore, each connector further comprising:
a threaded bore extending from a surface of the connector and intersecting the bore; and
a set screw threadably engaged with the threaded bore, the set screw and threaded bore cooperating to prevent relative movement between the flexible element and connector.

3. The spinal stabilization apparatus of claim 1, wherein each of the legs project from the base portion at an angle of approximately 90 degrees.

4. The spinal stabilization apparatus of claim 1, wherein the legs project from the base portion so as to converge toward each other in a direction away from the base portion.

5. The spinal stabilization apparatus of claim 4, wherein each of the legs project from the base portion at an angle between approximately 85 degrees and 90 degrees.

6. The spinal stabilization apparatus of claim 1, wherein the intermediate body portion includes a lower surface and a pair of side surfaces, wherein each of the side surfaces project from the lower surface at an angle of approximately 90 degrees.

7. The spinal stabilization apparatus of claim 1, wherein the intermediate body portion includes a lower surface and a pair of side surfaces, wherein the side surfaces project from the lower surface so as to converge toward each other in a direction away from the lower surface.

8. The spinal stabilization apparatus of claim 7, wherein each of the side surfaces project from the lower surface at an angle between approximately 85 degrees and 90 degrees.

9. The spinal stabilization apparatus of claim 1, further comprising:
 a retainer for selectively retaining a connector with a vertebral anchor, the retainer comprising:
 a retaining clip; and
 a retaining notch formed in the head portion of the vertebral anchor, wherein the retaining clip and retaining notch cooperate to prevent movement of the connector away from the anchor.

10. The spinal stabilization apparatus of claim 1, wherein each of the vertebral anchors is a bone screw.

11. A spinal stabilization apparatus, comprising:
 at least two vertebral anchors, each vertebral anchor having a head portion and a bone attachment portion extending from the head portion along an axis, the head portion including a base portion and a pair of spaced apart legs extending from the base portion to an upper extent of the legs and defining a channel therebetween, each vertebral anchor securable to a respective vertebra of a spine;
 a flexible element extendable between the vertebral anchors;
 at least two connectors each securable to the head portion of a respective vertebral anchor and each positionable on the flexible element; and
 a first spacer positionable between adjacent connectors and having a first and second end face,
 wherein at least one of the connectors includes a first body portion, a second body portion, an intermediate body portion extending between the first body portion and the second body portion, and a bore having a longitudinal axis which extends through each of the first body portion, the second body portion, and the intermediate body portion, the first body portion having a first outer surface that confronts the first end face of the first spacer, the first outer surface forming an angle with respect to the axis of the bone attachment portion of the vertebral anchor for enhancing the contact area between the first outer surface and the first end face of the first spacer when the connector is secured to the head portion;
 wherein the intermediate body portion is received in the channel of the head portion of a respective vertebral anchor by movement of the connector in a direction parallel to the axis of the bone attachment portion such that a lower surface of the intermediate body portion is engaged against the base portion, and the legs extend above an upper surface of the intermediate body portion with the lower surface of the intermediate body portion engaged against the base portion.

12. The spinal stabilization apparatus of claim 11, wherein the first outer surface is angled inward toward the axis of the bone attachment portion in a direction from the lower surface toward the upper surface.

13. The spinal stabilization apparatus of claim 11, wherein the first outer surface is angled outward away from the axis of the bone attachment portion in a direction from the lower surface toward the upper surface.

14. The spinal stabilization apparatus of claim 11, wherein the second body portion of the at least one connector has a second outer surface that confronts an end face of a second spacer, the second outer surface forming an angle with respect to the axis of the bone attachment portion of one of the vertebral anchors for enhancing the contact area between the second outer surface and the end face of the second spacer.

15. The spinal stabilization apparatus of claim 14, wherein the angles of the first and second outer surfaces with respect to the axis of the bone anchor portion of the vertebral anchor are different.

16. A method of stabilizing a spine within a body of a patient, comprising:
 securing at least first and second anchors to respective first and second vertebrae of the spine, each anchor having a head portion and a bone attachment portion extending from the head portion along a central axis, the head portion including a base portion and a pair of spaced apart legs extending from the base portion to an upper extent of the legs and defining a channel therebetween;
 assembling a flexible assembly outside of the body based on the position of the first and second anchors, the assembly including a spacer positioned between a first connector and a second connector, the spacer including a longitudinal axis and each of the first and second connectors including a longitudinal axis, the first connector including a first body portion, a second body portion, an intermediate body portion extending between the first body portion and the second body portion, and a bore which extends along the longitudinal axis of the first connector through each of the first body portion, the second body portion, and the intermediate body portion, the second connector including a first body portion, a second body portion, an intermediate body portion extending between the first body portion and the second body portion, and a bore which extends along the longitudinal axis of the second connector through each of the first body portion, the second body portion, and the intermediate body portion;
 inserting the intermediate body portion of the first connector in the channel of the head portion of the first anchor in a direction parallel to the central axis of the first anchor such that the upper extent of the legs of the head portion of the first anchor extend above an upper extent of the first connector with the intermediate body portion engaged against the base portion of the head portion of the first anchor;
 inserting the intermediate body portion of the second connector in the channel of the head portion of the second anchor in a direction parallel to the central axis of the second anchor; and
 coupling the first and second connectors of the flexible assembly to the anchors secured to the vertebrae of the spine to stabilize the spine such that the longitudinal axis of the spacer is non-parallel to the longitudinal axis of at least one of the first and second connectors.

17. The method of claim 16, wherein the assembling the flexible assembly outside the body step further comprises:

slidably mounting the first and second connectors on a cord; and slidably mounting the spacer on the cord so as to be positioned between the connectors.

18. The method of claim 17, further comprising pre-tensioning the cord to a desired amount.

19. The method of claim 17, wherein the assembling the flexible assembly outside the body step further comprises spatially fixing the connectors relative to the cord.

20. The method of claim 17, wherein the assembling the flexible assembly outside the body step further comprises adjusting a length of the spacer.

21. The method of claim 16, wherein the coupling the first and second connectors of the flexible assembly to the anchors step further comprises securing a retaining clip to each anchor to couple the flexible assembly to the anchors.

22. A spinal stabilization apparatus, comprising:
a first vertebral anchor including a head portion and a bone attachment portion extending from the head portion along a central axis, the head portion including a base portion and a pair of spaced apart legs extending from the base portion to an upper extent of the legs and defining a channel therebetween;
a flexible assembly removably securable to the first vertebral anchor, the flexible assembly comprising:
i) a flexible element;
ii) a first connector positionable on the flexible element for coupling with the head portion of the first vertebral anchor, the first connector including a first body portion, a second body portion, an intermediate body portion extending between the first body portion and the second body portion, and a bore having a longitudinal axis which extends through each of the first body portion, the second body portion, and the intermediate body portion for receiving the flexible element, the intermediate body portion including a lower surface and an upper surface opposite the lower surface, the first and second body portions extending transversely outward from the intermediate body portion; and
iii) a spacer positionable on the flexible element, the spacer including a first end surface, a second end surface and a bore having a longitudinal axis extending therethrough for receiving the flexible element, the first end surface of the spacer being in abutting contact with an end surface of the first body portion of the first connector such that the longitudinal axis of the spacer is non-parallel to the longitudinal axis of the first connector;
wherein the intermediate body portion of the first connector is received in the channel of the head portion of the first vertebral anchor by movement of the first connector in a direction parallel to the central axis such that the upper extent of the legs are positioned above the upper surface of the intermediate body portion of the first connector when the lower surface of the intermediate body portion of the first connector is engaged against the base portion, and the first body portion and the second body portion are disposed exterior to and on opposing sides of the head portion.

23. The spinal stabilization system of claim 22, wherein the flexible assembly further comprises a second connector positionable on the flexible element such that the spacer is positioned between the first connector and the second connector.

24. The spinal stabilization system of claim 23, further comprising a second vertebral anchor configured to be coupled to the second connector.

25. The spinal stabilization system of claim 22, wherein the end surface of the first body portion of the first connector converges toward an end surface of the second body portion of the first connector in a direction toward the upper surface of the intermediate body portion.

* * * * *